US009702802B2

(12) United States Patent
Ajay et al.

(10) Patent No.: US 9,702,802 B2
(45) Date of Patent: Jul. 11, 2017

(54) FILTER BYPASS

(75) Inventors: Kemal Ajay, Mount Waverley (AU);
Nitin Vayeda, Glen Waverley (AU)

(73) Assignee: Garrett Thermal Systems Limited, Berkshire (GB)

( * ) Notice: Subject to any disclaimer, the term of this patent is extended or adjusted under 35 U.S.C. 154(b) by 1060 days.

(21) Appl. No.: 13/582,832

(22) PCT Filed: Mar. 4, 2011

(86) PCT No.: PCT/AU2011/000254
§ 371 (c)(1),
(2), (4) Date: Nov. 19, 2012

(87) PCT Pub. No.: WO2011/106850
PCT Pub. Date: Sep. 9, 2011

(65) Prior Publication Data
US 2013/0061659 A1   Mar. 14, 2013

(30) Foreign Application Priority Data

Mar. 5, 2010 (AU) .................................. 2010900938

(51) Int. Cl.
*G01N 15/06* (2006.01)
*G01N 1/22* (2006.01)
(Continued)

(52) U.S. Cl.
CPC ........... *G01N 15/06* (2013.01); *G01N 1/2205* (2013.01); *G08B 17/10* (2013.01); *G08B 17/113* (2013.01); *G01N 2015/0693* (2013.01)

(58) Field of Classification Search
CPC .............................. G01N 15/06; G01N 1/2205
See application file for complete search history.

(56) References Cited

U.S. PATENT DOCUMENTS 6,285,291 B1   9/2001 Knox et al.
8,118,918 B2   2/2012 Knox et al.
(Continued)

FOREIGN PATENT DOCUMENTS

JP   59192940 A    11/1984
JP   61-048023 U    3/1986
(Continued)

OTHER PUBLICATIONS

"International Application No. PCT/AU2011/000254, International Search Report mailed Apr. 8, 2011", (Apr. 8, 2011), 3 pgs.
(Continued)

*Primary Examiner* — Lisa Caputo
*Assistant Examiner* — Punam Roy
(74) *Attorney, Agent, or Firm* — Schwegman Lundberg & Woessner, P.A.

(57) ABSTRACT

There is described a filter arrangement for a particle detector for detecting particles in an environment. The particle detector can include one or more sensors for analyzing fluid in a detection region to produce sensor output. The filter arrangement includes structure defining flow paths, for conveying fluid from the environment towards the detection region, including a first flow path, which includes a filter, and a second flow path bypassing the filter. There is also provided a mechanism for controlling relative flow rates of fluid through the first flow path and the second flow path and a controller configured to receive the sensor output corresponding to at least two relative flow rates and apply logic thereto to generate an output indicative of a condition of the filter.

34 Claims, 5 Drawing Sheets

(51) Int. Cl.
*G08B 17/10* (2006.01)
*G08B 17/113* (2006.01)

(56) References Cited

U.S. PATENT DOCUMENTS

| | | | |
|---|---|---|---|
| 2007/0176783 A1* | 8/2007 | Knox | G08B 29/145 340/607 |
| 2009/0084164 A1 | 4/2009 | Lowery | |
| 2010/0206043 A1* | 8/2010 | Tewarson | G01N 1/26 73/23.41 |
| 2016/0319726 A1* | 11/2016 | Otsuki | G01N 1/2252 |

FOREIGN PATENT DOCUMENTS

| | | |
|---|---|---|
| JP | 62-203437 U | 12/1987 |
| JP | H04-052519 | 2/1992 |
| JP | 04-303736 A | 10/1992 |
| JP | 08-206540 A | 8/1996 |
| JP | H08-271425 | 10/1996 |
| JP | 10-309422 A | 11/1998 |
| JP | 2000-509535 A | 7/2000 |
| JP | 2002-357117 A | 12/2002 |
| JP | 2003-056898 A | 2/2003 |
| JP | 2004-74859 A | 3/2004 |
| JP | 2006-250661 | 9/2006 |
| JP | 2009-527741 A | 7/2009 |
| NZ | 250497 A | 3/1998 |
| WO | WO-97/42486 A1 | 11/1997 |
| WO | WO-2007095675 A1 | 8/2007 |

OTHER PUBLICATIONS

"European Application Serial No. 11750097.5, extended European Search Report mailed Aug. 9, 2016", 8 pgs.

"International Application No. PCT/AU2011/000254, International Preliminary Report on Patentability mailed Sep. 20, 2012", 6 pgs.

"International Application No. PCT/AU2011/000254, Written Opinion mailed Apr. 8, 2011", 4 pgs.

"Japanese Office Action Serial No. 2016-001584, Office Action mailed Dec. 6, 2016", (w/ English Translation), 18 pgs.

* cited by examiner

FILTER BYPASS

PRIORITY CLAIM TO RELATED APPLICATIONS

This application is a national stage application under 35 U.S.C. § 371 of PCT/AU2011/000254, filed Mar. 4, 2011, and published as WO 2011/106850 A1 on Sep. 9, 2011, which claims priority to Australian Application No. 2010900938, filed Mar. 5, 2010, which applications and publication are incorporated by reference as if reproduced herein and made a part hereof in their entirety, and the benefit of priority of each of which is claimed herein.

FIELD OF THE INVENTION

The invention relates to particle detection. The following description focuses on smoke detectors, and in particular optical smoke detectors, however the skilled person will appreciate that the invention has broader application.

For the avoidance of doubt, 'particle detection' and like terms are used herein to refer to the detection of solid and/or liquid particles.

BACKGROUND OF THE INVENTION

Particle detectors are often used to warn of the presence of smoke emanating from a potential or incipient fire.

Smoke detectors operate in a variety of environments and include, for example, office environments, factories and manufacturing plant, power stations and clean rooms. Each of which has different levels of background particulate material. In some environments the concentration of background particulate matter will change from time to time.

A problem can be encountered with such smoke detection apparatus if they are continuously exposed to the relatively high levels of background pollution in the air that can exist in some environments. A large-scale example in recent years has been the high levels of smoke pollution often present in regions of Asia, which is largely attributable to the burning of brown coal.

Background pollution can cause contamination of components within the detector leading to premature failure, for example due to clogging of air paths or changes in the optical properties of the critical components within the detection chamber.

Scattering light detectors include a light source arranged to project a beam across the detection chamber. A photoelectric sensor is arranged so that its field of view is traversed by a portion of the beam. The photoelectric sensor receives light scattered from the beam due to the presence of particles in the detection chamber. Over time dust and debris can accumulate on surfaces within the detection chamber and reflect light towards the photoelectric sensor thereby providing a false indication of particles in the detection chamber. Dust and debris may also settle on the light source and/or the photoelectric sensor thereby obscuring the transmission and receipt of light and reducing the sensitivity of the detector.

One approach to addressing these problems involves the use of an 'air barrier'. An air barrier is created by directing one or more streams of clean air into the detection chamber to flow over the critical components, such as the light source, the photoelectric sensor and walls within the field of view of the photoelectric sensor, to prevent dust and debris accumulating thereon.

Aspirated smoke detectors employ a fan, known as an aspirator, to draw air to be studied through the detection chamber. The air to be studied enters the chamber via an inlet(s). A desirable implementation of the air barrier concept employs a filter(s) to create the clean air. The filter is arranged in parallel to the inlet, whereby the clean air is drawn through the filter and into the detection chamber by the aspirator. A common stream of air, e.g. from a network of pipes, may be divided into two portions—one portion being filtered to create the clean air, and the other portion entering the chamber to be studied.

Another approach to addressing the problems associated with the accumulation of dust and debris in the detection chamber is to obtain a measurement associated with light reflected from the accumulated dust and debris, known as 'background light', and to adjust the detection criteria applied to the signal received from the photoelectric sensor in response to the background light. One approach to obtaining a measure of background light involves the use of a second photoelectric sensor within the detection chamber. The second photoelectric sensor is arranged so that its field of view does not include the beam. Signals from the second photoelectric sensor are thereby indicative of light reflected within the detection chamber rather than light scattered directly from the beam.

The abstract of Japanese patent application 59192940 entitled "Smoke Meter with Purging Device" describes filling a measuring device with clean air and measuring opaqueness in the clean atmosphere to perform calibration. The described device includes a dedicated blower to supply clean air to the detection chamber. A valve controlled by depressible switches is used to close the intake tube to halt the flow of discharge gases to the detection chamber prior to the purging operation.

New Zealand patent 250497 is concerned with preventing fire suppression measures being activated in response to false alarms. It describes an operating syntax applicable to aspirated smoke detectors. When an alarm condition is detected the chamber is purged with clean air and a background 'smoke' signal is measured. If the background reading does not fall below a predetermined threshold a detector fault is indicated. If the background 'smoke' falls below the predetermined threshold, the system waits for the detected smoke level to rise above a further threshold before triggering the fire suppression systems.

Other attempts to overcome the problems associated with operating particle detectors in polluted environments have included dust filters placed in the airstream. Dust filters have been used to filter out particles not associated with the smoke to be detected. Smoke particles may occur in a variety of sizes depending on the fuel used and combustion conditions, and the filter type is chosen according to the type of dust particles expected and the type of smoke to be detected.

As conventional dust filters clog they begin to remove more particles from the air and eventually begin filtering out smoke particles (or other small particles of interest). This may be due to effective pore size of the filter being reduced as more particles clog the filter. Certain types of filters, particularly foam fitters, can start removing smoke particles before the pressure drop across, or flow rate through, the filter changes appreciably. The result is that the filter may be removing an unknown proportion of smoke long before clogging of the filter is detectable using pressure and/or flow measuring devices.

In some situations attempts have been made to condition the air sample prior to its introduction into the smoke detector e.g. by diluting the sample flow with clean air. The object of such dilution is to deliver to the detection chamber a sample flow with an unchanged particle distribution, but with a lower particle concentration than the original sample flow. Whilst such dilution arrangements go some way to addressing the problems associated with operating in a polluted environment, the lower particle concentration reduces the sensitivity and accuracy of the detector.

Dilution presents problems for air sampling smoke detectors that use a pipe network to draw air from a space being monitored, in that the introduction of the diluent air flow into the flow entering the detector reduces the amount of sample air drawn from the region being monitored. This causes an increase in the time taken for the sample air to travel from the region being monitored to the smoke detector, referred to as "transparent time", and consequently increases detection time.

The applicant has proposed, in their international patent application WO 2007/095675, an arrangement wherein a first portion of a sample flow is filtered through a HEPA (high efficiency particulate air) filter. The HEPA filter removes substantially all particles from the first portion of the sample flow to form clean air. The clean air is used to dilute a second, unfiltered, portion of the sample flow. The diluted sample flow is in turn carried to a detection region. This arrangement effectively addresses the transit time problem associated with other dilution arrangements and has a desirable 'fail safe' operation in that if the filter is allowed to clog to an extent that it becomes more restrictive to flow, the detection region will see an increase, rather than a decrease, in the concentration of particles. The extent of dilution may also vary due to environmental factors such as temperature and humidity. The changing dilution ratio reduces the accuracy of the associated smoke detector.

Despite these various advances in the art, the known filtration arrangements and dilution arrangements result in a reduced concentration of particles arriving at the detection region and can reduce the sensitivity and accuracy of the particle detector. It is of course desirable that a smoke detector should be sensitive and accurate. It is also desirable that if a filter is used, that it's condition, and in particular whether it has clogged to an extent that it is removing particles of interest (e.g. smoke particles), is known.

Objects of the invention include providing improved particle detection, an improved particle detector and components therefor, or at least providing alternatives for those concerned with particle detection.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

One aspect of the invention provides a filter arrangement for a particle detector for detecting particles in an environment, the particle detector including one or more sensors for analysing fluid in a detection region to produce sensor output, the filter arrangement including structure defining flow paths, for conveying fluid from the environment towards the detection region, including a first flow path, which includes a filter, and a second flow path bypassing the filter; a mechanism for controlling relative flow rates of fluid through the first flow path and the second flow path; and a controller configured to receive the sensor output corresponding to at least two relative flow rates and apply logic thereto to generate an output indicative of a condition of the filter.

The sensor output is preferably indicative of particle concentration.

In preferred forms of the invention, the mechanism is configured or controlled (e.g. controlled by the controller) to vary the relative flow rates, and the controller is configured to produce the output indicative of the condition of the filter, periodically (e.g. at fixed intervals, randomly from time to time, or according to a predetermined schedule) and/or in response to a sensed variation in particle concentration.

The controller may be configured to generate a fault signal if the condition of the filter exceeds a predetermined threshold.

The mechanism is preferably configured or controlled to vary the relative flow rates based on a predicted level of pollution in the environment to control the concentration of pollution reaching the detection region.

Another aspect of the invention provides a filter arrangement for a particle detector for detecting particles in an environment, the particle detector including one or more sensors for analysing fluid in a detection region to produce sensor output, the filter arrangement including, structure defining flow paths, for conveying fluid from the environment towards the detection region, including a first flow path, which includes a filter, and a second flow path bypassing the fitter, and a mechanism for controlling relative flow rates of fluid through the first flow path and the second flow path; the mechanism being configured or controlled to vary the relative flow rates based on a predicted level of pollution in the environment to control the concentration of pollution reaching the detection region.

In preferred forms of the invention the varying the relative flow rates based on the predicted level of pollution includes varying the relative flow rates based on a repeating schedule. Most preferably the schedule includes a night mode, in which a relatively lower proportion of fluid passes through the first flow path for relatively higher detector sensitivity, and a day mode in which a relatively higher proportion of fluid passes through the first flow path for reduced contamination of the detection region.

Optionally the mechanism is configured or controlled to periodically temporarily increase the relative flow rate through the second flow path to periodically increase sensitivity of the detector whereby a time averaged exposure of the detection region to fluid from the second flow path, and contaminants carried thereby, is reduced for reduced contamination of the detection region.

Another aspect of the invention provides a filter arrangement for a particle detector for detecting particles in an environment, the particle detector including one or more sensors for analysing fluid in a detection region to produce sensor output, the filter arrangement including: structure defining flow paths, for conveying fluid from the environment towards a detection region, including a first flow path, which includes a filter, and a second flow path bypassing the filter; a mechanism for controlling relative flow rates of fluid through the first flow path and the second flow path; and a controller configured to control the mechanism to periodically temporarily increase the relative flow rate through the second flow path to periodically increase sensitivity of the detector whereby a time averaged exposure of the detection region to fluid from the second flow path, and contaminants carried thereby, is reduced for reduced contamination of the detection region.

In preferred forms of the invention the relative flow rate through the second flow path is temporarily increased one or more times per minute.

Preferably the mechanism is configured or controlled such that, during each periodic temporary increase in relative flow rate through the second flow path, substantially all of the fluid is conveyed via the second flow path. Most preferably the mechanism is configured or controlled such that, between each periodic temporary increase in relative flow rate through the second flow path, substantially all of the fluid is conveyed via the first flow path.

The structure may include a flow splitting arrangement to receive a common stream of fluid from the environment and direct respective portions of the stream into the first flow path and the second flow path. Preferably the structure includes a flow combining arrangement to receive fluid from the first flow path and the second flow path and convey a combined stream of fluid toward the detection region.

The mechanism may include a valve, e.g. a solenoid valve. In preferred forms of the invention the mechanism includes an electro-mechanical device.

Preferably the structure and mechanism together impose a flow restriction substantially greater than a flow restriction imposed by the filter whereby the relative flow rates through the first flow path and the second flow path are substantially independent of filter condition. Preferably the filter is a HEPA filter.

In preferred forms of the invention the second flow path is configured such that fluid carried thereby is substantially unfiltered of particles of interest.

Another aspect of the invention provides a particle detector, for detecting particles in an environment, including: structure defining a detection region; one or more sensors for analysing fluid in the detection region to produce sensor output; and the above filter arrangement arranged to convey fluid, from the environment to the detection region, and to cooperate with the sensors.

Preferably the particle detector includes a controller having a purge mode in which the controller controls the mechanism to deliver fluid to the detection region substantially only from the first flow path to purge the detection region of fluid from the second flow path, and a detection mode in which the controller controls the mechanism to deliver at least some fluid from the second flow path to the detection region; and being configured to apply logic to sensor output from the detection mode to generate a further output; and if necessary adjust the logic, based on the sensor output from the purge mode, to compensate for contamination of the detection region.

Another aspect of the invention provides a particle detector, for detecting particles in an environment, including structure defining flow paths, for conveying fluid from the environment towards a detection region, including a first flow path, which includes a filter, and a second flow path bypassing the filter, a mechanism for controlling relative flow rates of fluid through the first flow path and the second flow path; and one or more sensors for analysing fluid in the detection region to produce sensor output; and a controller having a purge mode in which the controller controls the mechanism to deliver fluid to the detection region substantially only from the first flow path to purge the detection region of fluid from the second flow path, and a detection mode in which the controller controls the mechanism to deliver at least some fluid from the second flow path to the detection region; and being configured to apply logic to sensor output from the detection mode to generate a further output; and if necessary adjust the logic, based on the sensor output from the purge mode, to compensate for contamination of the detection region.

The controller is preferably configured to periodically (e.g. at fixed intervals, randomly from time to time, or according to a predetermined schedule) transition between the purge and detection modes. Most preferably the controller is configured such that the transition from the detection mode to purge mode is conditional on the sensor output.

The controller may store a plurality of measurements based on the sensor output over an interval of time when the chamber is purged. In preferred forms of the invention the controller is configured to apply further logic, to the sensor output when the chamber is purged, and if necessary generate fault signal.

The logic may include subtracting a measure of background light from the sensor output. Adjusting the logic may include calculating and substituting a new measure of background light.

The sensors include one or more photoelectric devices.

Another aspect of the invention provides a particle detection system for detecting particles in an environment including plumbing defining at least one inlet, for receiving fluid from the environment, and at least one outlet; an aspirator between the inlets and the outlet to move fluid through the plumbing; and the above particle detector arranged to receive fluid from downstream of the aspirator and deliver fluid upstream of the aspirator whereby fluid is moved through the particle detector by the aspirator.

Another aspect of the invention provides a filter arrangement for receiving sample fluid and supplying fluid to be moved through a detection region of a particle detector, the filter arrangement including structure defining a first flow path and a second flow path, a controllable mechanism for controlling relative flow rates of received sample fluid through the first flow path and the second flow path, and a controller; at least the first flow path including a filter for filtering particles from fluid travelling along the first flow path; the first, filtered, flow path and the second flow path being arranged in parallel, such that fluid travelling along the second flow path bypasses the filter, the first, filtered, flow path and the second, bypass, flow path being arranged to communicate downstream of the filter with the detection region; the controllable mechanism having at least two modes, the at least two modes corresponding to differing relative flow rates through the first, filtered, flow path and the second, bypass, flow path; and the controller being configured or programmed to receive at least one parameter characterising the fluid for each of the at least two modes, and being configured or programmed to apply logic to generate a filter condition signal indicative of filter condition based on the received parameters.

The at least one parameter is preferably a signal indicative of particle concentration, which is most preferably received from components of the particle detector associated with the detection region, e.g. a photoelectric device.

According to preferred forms of the invention, the first, filtered, flow path and the second, bypass, flow path converge downstream of the filter and are subsequently communicated with the detection region.

The controllable mechanism is preferably a valve. The controllable mechanism may be an electro-mechanical device. According to preferred forms of the invention the controllable mechanism is a solenoid valve. Preferably the controllable mechanism is operatively associated with the controller whereby the controller switches between the at least two modes. This allows the controller to be configured or programmed to switch between the at least two modes to produce said filter condition signal. For example, the controller may be configured or programmed to periodically, say once every week, produce said filter condition signal.

The controller may be configured or programmed to switch between the modes based on actual or predicted pollution levels to control the concentration of pollution reaching the detection region. For example, one mode, wherein substantially all of the received sample fluid is filtered, might be used during day time operation in a factory environment (when high pollution levels are expected), and a second mode, wherein substantially all of the received sample fluid travels along the bypass line, used at night. In this way the particle detector can operate at full sensitivity at night, yet be protected from day time pollution. The controller may have three or more modes corresponding to differing levels of filtration.

Optionally the controller may be configured or programmed to change between modes to produce the filter condition signal in response to a signal indicative of variation in particle concentration, e.g. if a rapid increase or decrease (e.g. a 50% decrease) in particle concentration is detected, the controller may control the controllable mechanism to obtain said filter condition signal and thereby determine whether the rapid increase or decrease is associated with a change in the received sample fluid or a change in the filter condition. The controller may also be configured or programmed to change between modes in response to a signal indicative of particle concentration for increased detector sensitivity or increased pollution protection.

Preferably, one of the at least two modes, referred to as a filter-check mode, corresponds to substantially all of the received sample fluid travelling along the second, bypass, flow path.

According to preferred embodiments of the invention, in at least one of the at least two modes, the structure and/or the controllable mechanism impose a flow restriction substantially greater than a flow restriction imposed by the filter whereby the relative quantity of fluid flowing through the first, filtered, flow path and other flow path(s) is substantially independent of filter condition.

The controller of preferred forms of the invention is configured or programmed to apply logic to generate a fault signal if the filter condition signal exceeds a predetermined threshold.

The structure may include a flow splitting arrangement configured to receive, e.g. through a common opening, a common stream of sample fluid, e.g. from a common pipe associated with a piping network, and direct respective portions of the stream into the first, filtered, flow path and the second, bypass, flow path.

This aspect of the invention also provides a particle detector including the filter arrangement and a detection region, the filter arrangement being communicated with the detection region for supplying fluid thereto.

This aspect of the invention also provides a method of determining filter condition of a filter upstream of a particle detector, the method including: creating a first fluid flow through at least one of the filter and a bypass arranged to bypass the filter upstream of the particle detector, measuring at least one first parameter associated with the first fluid flow; varying the relative flow rates through the filter and the bypass to generate a second fluid flow; measuring at least one second parameter associated with the second fluid flow; and applying logic to the measured parameters to determine filter condition.

The measured parameters are preferably particle concentration, and are most preferably measured at the particle detector.

The varying preferably includes actuating at least one electro-mechanical valve.

According to preferred forms of the invention, the first and second fluid flows are conveniently created by selectively preventing and allowing the flow of fluid through the bypass.

In another aspect the invention provides a filter arrangement for receiving sample fluid and supplying fluid to be moved through a detection region of a particle detector, the filter arrangement including, structure defining a first flow path and a second flow path, a controllable mechanism for controlling relative flow rates of received sample fluid through the first flow path and the second flow path, and a controller; at least the first flow path including a filter for filtering particles from fluid travelling along the first flow path; the first, filtered, flow path and the second flow path being arranged in parallel, whereby fluid travelling along the second flow path bypasses the filter, the first, filtered, flow path and the second, bypass, flow path being arranged to communicate downstream of the filter with the detection region; the controllable mechanism having at least two modes, the at least two modes corresponding to differing relative flow rates through the first, filtered, flow path and the second, bypass, flow path; and the controller being configured or programmed to switch between the modes based on actual or predicted pollution levels to control the concentration of pollution reaching the detection region.

This aspect of the invention also provides a particle detector including the filter arrangement and a detection region, the filter arrangement communicating with the detection region for supplying fluid thereto.

This aspect of the invention also provides a method of controlling the concentration of pollution in fluid supplied to a detection region of a particle detector, the method including the steps of: creating a fluid flow through at least one of a filter and a bypass arranged to bypass the filter, directing the fluid flow to the detection region; and varying the relative flow rates through the filter and the bypass based on actual or predicted pollution levels to control the concentration of pollution reaching the detection region.

In broad terms a further aspect of the invention is directed towards a method of monitoring an aspirated smoke/particle detector (in a polluted environment) including: providing a first flow path between a sampled air output and a detection zone of the smoke/particle detector, the first flow path having a filter providing a second flow path between the sampled air output and the detection zone which bypasses the first, filtered, flow path obtaining a first signal associated with particle concentration in the first filtered flow path diverting sampled air through the second flow path obtaining a second signal associated with particle concentration in the second flow path obtaining a measurement representative of the condition of the filter based on the first and second signals.

The invention further provides a method of operating an aspirated particle detector including: monitoring an aspirated smoke/particle detector(in a polluted environment) including: providing a first flow path between a sampled air output and a detection zone of the smoke/particle detector, the first flow path having a filter providing a second flow path between the sampled air output and the detection zone which bypasses the first filtered flow path switching between the first and second flow paths in response to a signal indicative of the generation of non-indicative particles (e.g. dust particles).

The signal indicative of the generation of non-indicative particles may be, for example, a timing signal or a detection signal.

In another aspect the invention provides a particle detector including, a detection region; one or more sensors for detecting, and providing a signal indicative of, particles in the detection region; structure defining a study fluid flow path for conveying study fluid to the detection region; a controllable mechanism for controlling a flow rate along the study fluid flow path; and a controller configured to control the controllable mechanism to selectively move study fluid through the detection region whereby the detection region is exposed to moving study fluid, and contaminants carried thereby, for reduced contamination of the detection region.

Preferably the structure further defines a sample fluid flow path, for conveying a stream of sample fluid drawn from a sample space, and the controllable mechanism is configured to direct at least a portion of the stream of sample fluid to flow along the study fluid flow path, said portion of the stream of sample fluid forming the study fluid.

According to preferred embodiments of the invention, the structure further defines a first, filtered, flow path, the study fluid flow path forming a second, bypass, flow path; each of the first, filtered, flow path and the second, bypass, flow path communicating with the detection region.

The particle detector preferably includes an aspirator downstream of the detection region to create, and move, said stream of fluid.

The second, bypass, flow path is preferably substantially unfiltered whereby the study fluid is substantially unfiltered.

The first, filtered, flow path is preferably configured to filter substantially all contaminates from the fluid travelling therealong. By way of example, the first, filtered, flow path may be spanned by a HEPA filter.

Preferably the controller is configured to move study fluid through the detection region about 20% of the time. Most preferably study fluid is moved through the detection region one or more times per minute. By way of example, the detection region may be alternately exposed to filtered fluid from the first, filtered, flow path for 4 seconds and substantially unfiltered fluid from the second, bypass, flow path for 1 second.

The controller may be configured to receive the indicative signal and apply logic to generate a further signal. Preferably, the controller is configured to receive the indicative signal during the selective moving of study fluid through the detection region and if necessary, compensate for said contamination of the detection region.

This aspect of the invention also provides a method of operating an aspirated particle detector having a detection region, the method including the steps of: intermittently introducing a new sample flow to the detection chamber, selectively moving a study fluid through the detection region; and studying the study fluid in the detection region to generate a signal indicative of particle concentration; whereby the detection region is selectively exposed to moving study fluid, and contaminants carried thereby, for reduced contamination of the detection region.

Said selectively moving preferably includes periodically directing at least a portion, and more preferably substantially all, of a stream of fluid drawn from a sample space for reduced transit time. Said periodically directing preferably includes directing said stream portion from a first, filtered, flow path to a second, bypass, flow path; wherein each of the first, filtered, flow path and the second, bypass, flow path communicate with the detection region; the fluid travelling along the second, bypass, flow path forming the study fluid. The method preferably includes activating an aspirator downstream of the detection region to create, and move, said stream of fluid.

The second, bypass, flow path is preferably substantially unfiltered such that the study fluid is substantially unfiltered.

The first, filtered, flow path is preferably configured to filter substantially all contaminants from the fluid travelling therealong. By way of example, the first, filtered, flow path may be spanned by a NEPA filter.

Preferably the method includes moving a study fluid through the detection region about 20% of the time. Most preferably study fluid is moved through the detection region one or more times per minute. By way of example, the detection region may be alternately exposed to filtered fluid from the first, filtered, flow path for 4 seconds and substantially unfiltered fluid from the second, bypass, flow path for 1 second.

The method may include applying logic to the indicative signal to generate a further signal; and may also include receiving the indicative signal during the selective moving of study fluid through the detection region and if necessary compensating for said contamination of the detection region.

In another aspect the invention provides a particle detector including a detection region; one or more sensors for detecting, and providing a signal indicative of, particles in the detection region; a controller; structure defining a first flow path and a second flow path for conveying received sample fluid to the detection region; and a controllable mechanism for controlling relative flow rates of received sample fluid through the first flow path and the second flow path; at least the first flow path including a filter for filtering particles from fluid travelling along the first flow path; the first, filtered, flow path and the second flow path being arranged such that fluid travelling along the second flow path bypasses the filter; the controllable mechanism having a purge mode, wherein the detection region receives substantially only filtered fluid from the first, filtered, flow path to purge the detection region of unfiltered fluid, and a detection mode wherein the detection region receives at least some fluid from the second, bypass, flow path; the controller being configured or programmed to, when in the detection mode, receive the indicative signal and applying logic to generate a further signal; the controller being configured or programmed to receive the indicative signal when the detection region is purged of unfiltered fluid and if necessary adjust the logic in response thereto, whereby to compensate for contamination of the detection region.

The controller is preferably operatively associated with the controllable mechanism to control the transition between the purge and detection modes. The controller may be configured such that the transition from the detection mode to purge mode is conditional on the indicative signal. For example the detector may be configured to not enter the purge mode if the indicative signal is at or above a threshold. The start purge threshold preferably corresponds to a particle concentration less than, and most preferably about 50%, of an alarm threshold.

The controller preferably stores a plurality of measurements based on the indicative signal over an interval of time when the chamber is purged. The controller may be configured to generate a fault signal if the indicative signal when the chamber is purged is too low, too high, too variable, and/or too different from the indicative signal during the previous purging and adjusting operation. The logic may include subtracting a measure of background light from the indicative signal. The adjustment of the logic may include averaging the stored indicative signals to calculate a new measure of background light.

This aspect of the invention also provides a method of operating a particle detector having a detection region, the method including moving a study fluid through the detection region; studying the study fluid in the detection region to generate a signal indicative of particle concentration; and applying logic to the indicative signal to generate the further signal; filtering sample fluid drawn from a sample space to form filtered fluid; moving the filtered fluid through the detection region to purge the detection region of the study fluid; studying the filtered fluid in the detection region to generate a second signal indicative of particle concentration; and if necessary adjusting the logic in response to the second indicative signal whereby to compensate for contamination of the detection region.

Moving the filtered fluid through the detection region to purge the detection region of the study fluid may be conditional on the indicative signal.

As used herein, except where the context requires otherwise, the term "comprise" and variations of the term, such as "comprising", "comprises" and "comprised", are not intended to exclude further additives, components, integers or steps.

DETAILED DESCRIPTION OF THE EMBODIMENTS

Figure 1:
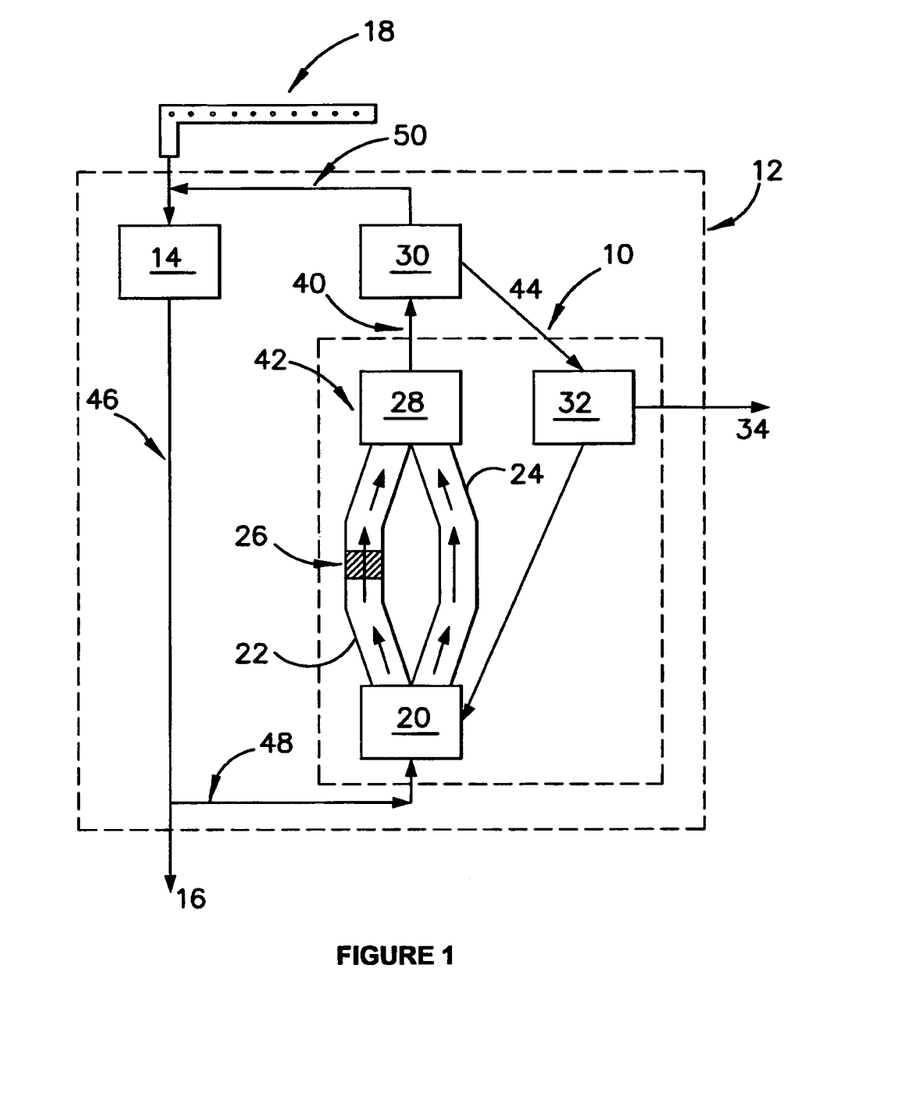
FIG. 1 is a schematic illustration of a particle detector in accordance with a preferred embodiment of the invention.

FIG. 1 illustrates a particle detector 12 in accordance with a preferred embodiment of the invention. The particle detector 12 includes a filter arrangement 10, a detection chamber 30 and an aspirator 14.

The aspirator 14 draws air from a piping network 18. This air is referred to as 'sample air'. The sample air is exhausted from the aspirator 14 via an exhaust pipe 46 to outlet 16. A sampling pipe 48 branches from the exhaust pipe 46 and extends to the filter arrangement 10 to communicate the filter arrangement 10 with the aspirator exhaust. A pipe 40 communicates the filter arrangement 10 with the detection chamber 30. The detection chamber 30 is in turn communicated with the aspirator inlet by pipe 50. Sample air from the aspirator exhaust is thereby driven through the filter arrangement 10, through the detection chamber 30, and returned to the aspirator inlet. This arrangement is referred to as a sub-sampling loop.

The fitter arrangement 10 includes structure 42 defining a first flow path 22 and a second flow path 24. The flow paths 22 and 24 are arranged in parallel and extend between a manifold space 20 and a plenum 28. Sample air from the aspirator exhaust is received within the manifold space 20 where it is divided between the first and second flow paths 22 and 24. The two flow paths converge and the flows are combined within the plenum 28. The combined flow is in turn conveyed to the detection chamber 30.

A filter 26 is positioned along the first flow path 22.

The manifold space 20 includes a valve forming a controllable mechanism for varying the relative flow rates through the first and second flow paths. The valve could be a simple flap or butterfly valve such as flap 120B illustrated in FIGS. 2A and 2B. By varying the operation of the valve, the relative portions of filtered and unfiltered air arriving at the plenum 28, and in turn the composition of the combined air arriving at the detection chamber 30, can be controlled.

The filter arrangement 10 further includes a controller 32. The controller 32 receives from the detection chamber 30 sensor output in the form signal 44 indicative of the concentration of particles within the detection chamber. In some embodiments the controller can be arranged to process the received signals to generate an output. In this embodiment the controller 32 operatively connected with the valve within manifold space 20 to control the relative flow rates through the first flow path 22 and the second flow path 24.

The "controller" as described herein can be any arrangement for receiving an input signal, and processing the signal to generate a further useful signal. For example the controller could include, but is not limited to, a microprocessor, field programmable gate array (FPGA), ASIC, microcontroller, or any functionally equivalent analogue or digital realisation.

The controller 32, based on the signal indicative of particle concentration 44, generates an alarm signal (not shown) when certain alarm criteria are met. As will be described, the controller 32 also applies logic to generate a signal 34 indicative of the condition of the filter 26.

Smoke detectors according to preferred forms of the invention may be installed along a fire alarm loop (not shown), wherein the signal 34 indicative of the condition of the filter is transmitted via the loop to a fire alarm control panel (FACP; not shown). The FACP may display the condition of filter and signal an error, e.g. by providing an audible signal or flashing light on a display, when the filter condition exceeds a predetermined threshold.

The filter 26 is configured to produce a known reduction in particle concentration. According to a preferred form of the invention, under the influence of controller 32, the valve within the manifold space 20 is positioned so that substantially all of the received sample air is directed through the first, filtered, flow path 22 when in a normal, detection, mode. Thereby substantially all of the air arriving at the detection chamber 30 is filtered. The detection chamber 30 is thus protected from pollution.

The alarm criteria applied to the signal 44 by controller 32 are adjusted based on the known reduction in particle concentration associated with the filter 26. According to the described preferred form of the invention, the adjustment is automatically performed by the controller 32, and the amount of adjustment is regularly updated based on the filter condition as determined by the following procedure.

Once a week, at a fixed time of day, the controller 32 sends a signal to the manifold space 20 to change the position of the valve therein to vary the relative flow rates through the first path 22 and the second path 24 such that substantially all of the received sample air is directed through the bypass flow path 24. Thereby substantially all of the fluid received by the detection chamber 30 is unfiltered. This condition is referred to as a 'filter check mode'.

By comparing the signal 44 in the normal, detection, mode and the filter check mode, the controller 32 is able to make an inference of the filter condition, and in particular the extent to which the filter 26 is filtering particles of interest from fluid passing there through.

In the described normal, detection, mode, the detection chamber 30 is protected from pollution, whilst the described adjustment maintains an improved degree of accuracy over other filtering arrangements. Nonetheless, by filtering the incoming air the particle concentration reaching the detection chamber 30 is reduced which results in some reduction in sensitivity compared to unfiltered arrangements.

According to preferred forms of the invention, the controller 32 is operative to control the valve within the manifold space 20 to vary the relative flow rates through the first flow path 22 and the second flow path 24, and thus control the extent to which fluid received by the detection chamber 30 is filtered, in response to actual or predicted pollution levels. When the relative flow rates are so adjusted, the controller 32 makes a corresponding adjustment to the alarm criteria. The invention thereby allows for maximum protection from pollution when the air is heavily polluted, and for maximum sensitivity when the air is not so polluted.

By way of example, the particle detector 12 might operate in the normal, detection, mode during the day time operation of a factory when pollution levels are expected to be high; and revert to a "night time" mode when the factory is inactive and the pollution levels should be lower. In the night time mode substantially all, or a selected fraction of, the received sample air is directed through the second, unfiltered, flow path of 24 and a corresponding adjustment to the alarm criteria is made by the controller 32. The detection chamber 30 is thereby protected from the day time pollution, whilst maximum sensitivity is maintained during the night. The controller 32 might compare the signals 44 on each transition between the normal, detection, mode and the night time mode. Thus the filter condition may be checked, and the alarm criteria appropriately updated, on a twice daily basis.

According to certain embodiments of the invention, a portion, or substantially all, of the received sample air may pass through the second, unfiltered, flow path 24 during normal operation for maximum sensitivity. According to these embodiments, the amount of filtration may be increased during a pollution event (e.g. the release of theatrical smoke within a theatre or a diesel powered train arriving at a station). The logic applied to the sensor output may be varied as a function of the relative flow rates, e.g. an alarm threshold or alarm delay might be lowered when the degree of filtration is increased. The variation in the amount of filtration might be controlled by a timetable (eg. a train timetable) or on other inputs. For example, in a simple implementation, an operator may provide an input to switch to a highly filtered mode before operating a piece of machinery known to produce a large volume of particle pollution. Certain embodiments may have more than two, e.g. four, discrete modes of operation corresponding to differing relative flow rates and thus differing amounts of filtration.

The degree of filtration may be adjusted in response to the detected particle concentration. By way of example, the filter 26 may be a foam filter selected to filter dust whilst allowing smoke particles to pass therethrough. According to this embodiment, the controller 32 responds to a signal 44 indicative of an increased concentration of particles by varying the relative flow rate through the flow paths 22 and 24 so that a greater portion of the received sample fluid is filtered. By monitoring the variation in the signal 44, the controller 32 can make an inference as to whether the detected increase in particle concentration is associated with dust or smoke.

Figure 2A:
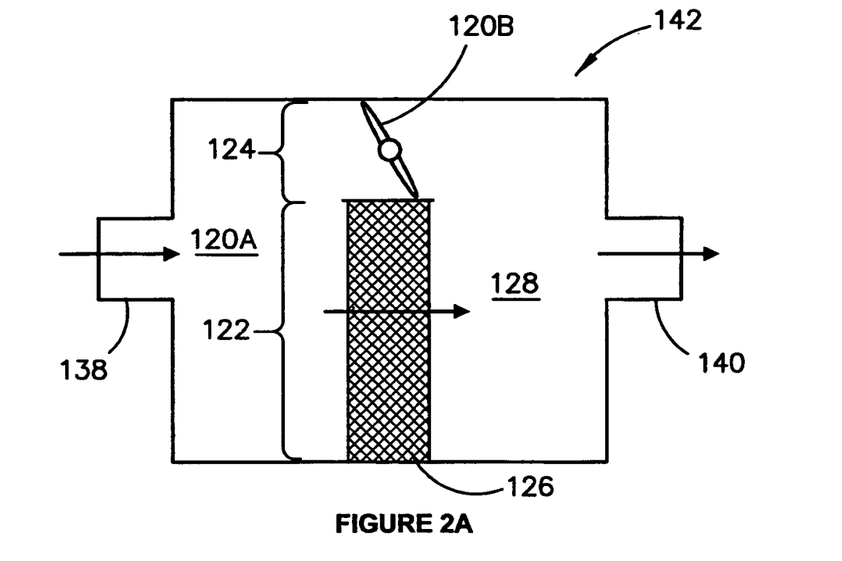
FIG. 2A is a schematic illustration of a filter arrangement according to a preferred embodiment of the invention in one operating mode.
Figure 2B:
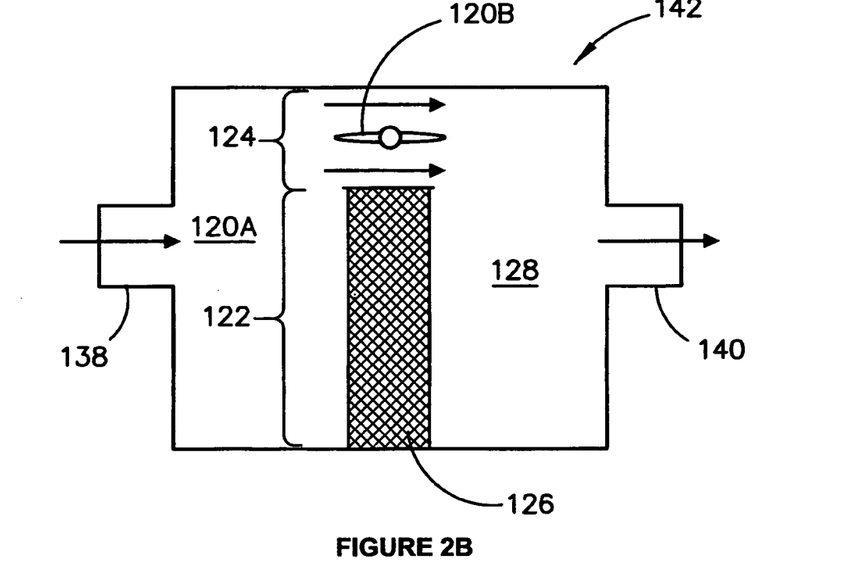
FIG. 2B is a schematic illustration of filter arrangement of FIG. 2A in another operating mode.

FIGS. 2A and 2B schematically illustrate the structure 142 of a filter arrangement in accordance with an embodiment of the invention. Sample air is received via an inlet 138 into a manifold space 120A. The structure defines two parallel flow paths, 122 and 124. The flow path 122 is spanned by a foam filter 126. The flow path 124 is spanned by a simple pivotally mounted flap forming a controllable mechanism for varying the flow rate through the flow path 124, and in turn the relative flow rates through the flow paths 122 and 124. FIG. 2A shows the flap 120B in the closed position. FIG. 2B shows the flap 120B in the open position. Flow paths 122 and 124 converge and the flows are thus combined in the plenum 128, the combined fluid exits the structure 142 via the outlet 140.

FIG. 2A illustrates an arrangement similar to the aforedescribed normal, detection, mode. The flow path 124 is closed by the flap 120B so that substantially all of the received flow is directed through the filter 126. The filter 126 has a relatively high impedance such that when the flap 120B is opened, as in FIG. 2B, substantially all of the flow is directed through the flow path 124.

Foam filters, such as filter 126, effectively filter out dust particles. Within their normal operating range, such filters remove only a small proportion of the smoke particles. The differential treatment of smoke and dust particles desirably allows for the detection chamber to be protected from dust with only a relatively small reduction in sensitivity. A problem with such foam filters is that as they clog, they begin filtering out smoke particles, and a significant portion of smoke particles may be filtered before there is any appreciable change in pressure drop across the filter. It is thereby difficult to determine when the filter has blocked to an extent that it is filtering out smoke particles. As the skilled person will appreciate, preferred embodiments of the invention address this problem by opening the flap 120B so that the detection chamber is exposed to unfiltered air.

The structure of FIGS. 1, 2A and 2B lend themselves to two further desirable operating modes.

According to a first of these two modes, the flap 120B, and thus the bypass 124, is opened and closed periodically. In this mode the detector receives periodic bursts of unfiltered air, separated by periods of clean air. This has the advantage of extending the detector life by reducing incoming contaminates in proportion to the duty cycle of the clean air. For example, if the unfiltered air were permitted to enter the detector for one second followed by exposure to the air from the filter 126 for four seconds, then the contamination rate of the downstream detector would be one fifth of the rate that would occur if the detector were fully exposed to the unfiltered air all of the time. This method offers the similar 
life-extending benefits as the dilution arrangement proposed by the applicant in their international patent application WO 2007/095675. However, preferred forms of this time-dependent method have the advantage that they do not rely on maintaining or measuring ratios of flow. According to preferred forms of the invention, the controller 32 simply applies normal processing techniques to the signal 44 when the chamber 30 is occupied by unfiltered air while ignoring signal 44 when the chamber 30 is occupied by filtered-air.

A second of these desirable operating modes is particularly well suited to the use of a NEPA filter which effectively filters out substantially all particles from the fluid flowing therethrough. When the flap 120B is closed such that all of the received sample fluid is directed through the filter 126, clean air (ie air devoid of particles, or at least devoid of particles of interest) is delivered to the detection chamber 30. Once the chamber is purged of any unfiltered air and filled with clean air, the signal 44 provides an indication of background light with the detection chamber. This detection chamber can be used to adjust the alarm criteria. By way of example a background light reading might be subtracted from the signal 44 (when the chamber 30 is flooded with unfiltered air) to generate a further signal, and an alarm sounded when the further signal exceeds a predetermined threshold.

Figure 3A:
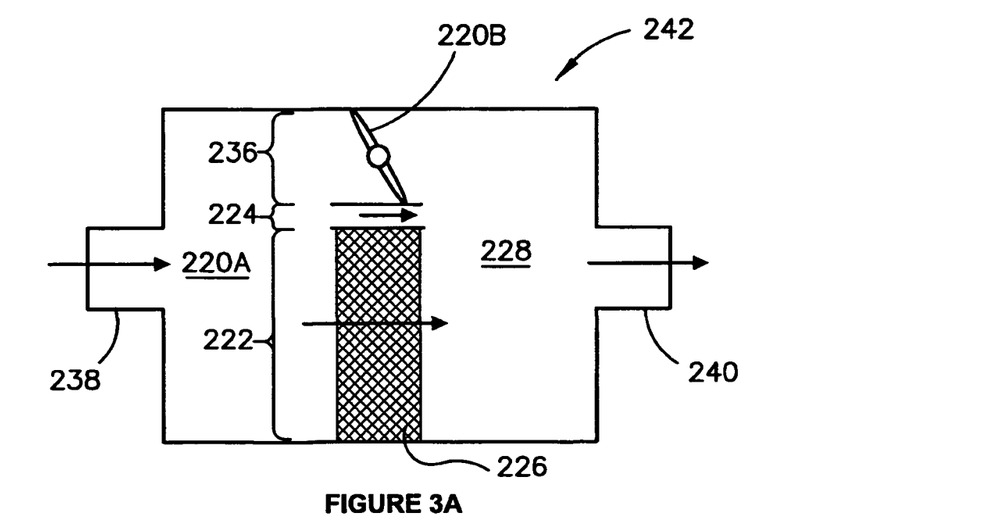
FIG. 3A is a schematic illustration of a filter arrangement according to a further embodiment of the invention in one operating mode.
Figure 3B:
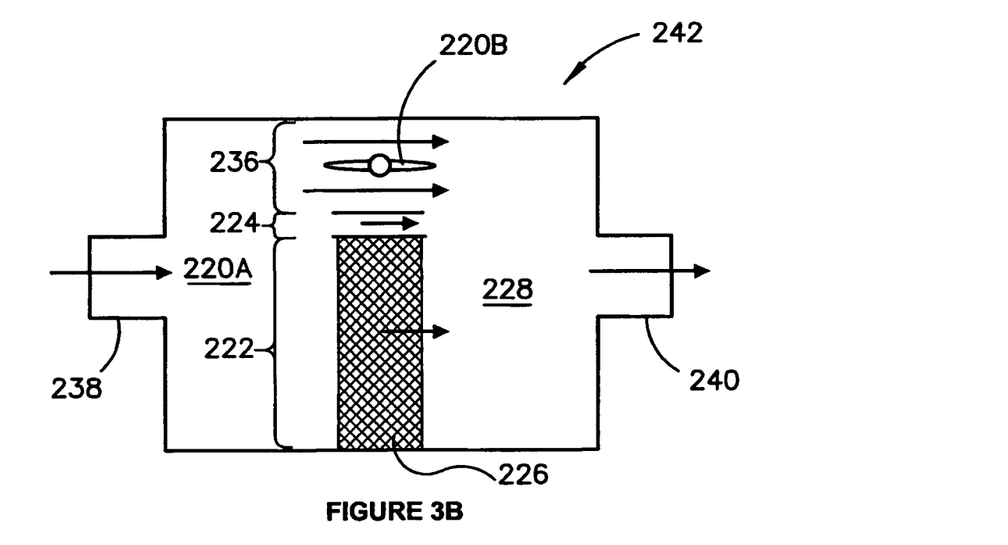
FIG. 3B is a schematic illustration of the filter arrangement of FIG. 3A in another operating mode.

FIGS. 3A and 3B schematically illustrate a further embodiment of the invention. This embodiment includes three parallel flow paths 222, 224 and 236. The flow path 222 is spanned by a HEPA filter. A second flow path 224 is unfiltered. A third flow path 236 is spanned by a flap 220B.

In a normal, detection, mode the flap 220B is dosed to close the flow path 236 as illustrated in FIG. 3A. Thereby substantially all of the sample air received via inlet 238 into manifold space 220A is divided between the flow paths 222 and 224. From the flow paths 222 and 224, the air is received into plenum space 228 and exits the structure 242 via the outlet 240. Accordingly to this arrangement, the relative flow rates through the paths 222 and 224 is determined by the relative impedance of those two flow paths.

Preferred forms of invention include one or more structural elements, such as an apertured baffle plate (not shown) arranged to control the relative impedance of the flow paths 222 and 224. The baffle plate preferably has an impedance significantly greater than that of the filter 226. The relative impedance of the two flow paths 222 and 224 is thereby dominated by the geometry of the baffle plate so that the relative flow rates are more or less independent of the filter condition (at least until the filter becomes extremely clogged). By way of example, the baffle plate may include a single small hole in communication with the unfiltered flow path 224, and several like holes in communication with the filtered flow path 222.

Moreover, this arrangement provides a 'failsafe' operation in that a filter clogged to an extent that its impedance changes appreciably (e.g. when recommended service intervals have been ignored) will generate a higher particle concentration signal. As the filter 226 clogs, the impedance of the flow path 222 increases and relatively more air flows through the flow path 224. Thus, as the filter 226 clogs, the air passing through the structure 242 in the normal, detection, mode becomes less filtered, ie. has a higher particle concentration.

As in the embodiment of FIGS. 2A and 2B, the flow path 236 desirably has an impedance significantly lower than that of the flow paths 222 and 224 so that when the flap 220B is opened, substantially all of the received fluid passes through the unfiltered flow path 236. Alternatively a further flap 320C, as illustrated in FIGS. 4A and 4B may be provided.

Periodically, or whenever the detected smoke reading changes by some value, the position of the flap 220B may be changed from the dosed position of FIG. 3A to the open position of FIG. 3B. In doing so, the smoke detector is now exposed to undiluted smoke and the detector will record the actual sampled smoke value. By forming the ratio from smoke levels taken in the two configurations shown in FIGS. 3A and 3B, it is possible to determine the actual dilution ratio of when in the normal, detection, mode (ie the ratio of the fluid travelling through the flow paths 222 and 224) and the threshold levels or sensitivity gain of subsequent analysing equipment may be adjusted.

A similar 'failsafe' operation could be achieved using the structure of FIGS. 2A and 2B by only partly closing the flap 120B in the normal, detection, mode.

Figure 4A:
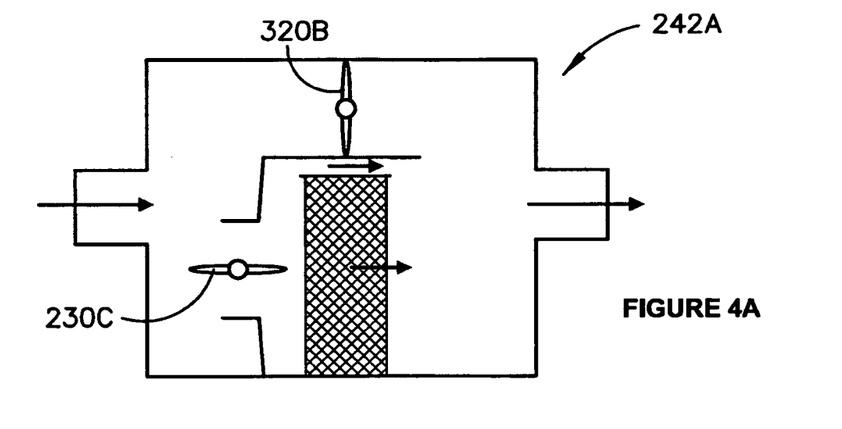
FIG. 4A is a schematic illustration of a filter arrangement according to a further embodiment of the invention in one operating mode.
Figure 4B:
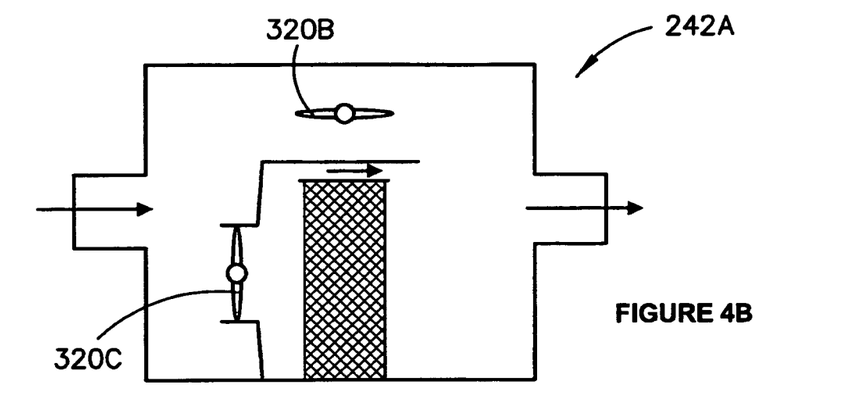
FIG. 4B is a schematic illustration of the filter arrangement of FIG. 4A in another operating mode.
Figure 5:
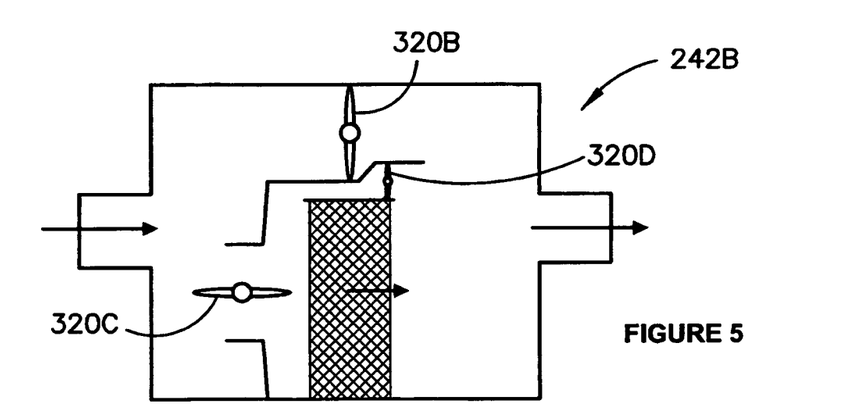
FIG. 5 is a schematic illustration of a filter arrangement according to a further embodiment of the invention in one operating mode.

The embodiment of FIGS. 4A and 4B might be modified by the inclusion of a third valve 320D to selectively close flow path 224 and filter 226 being a HEPA filter as illustrated in FIG. 5. By closing flow paths 224 and 236 all of the air is filtered such that a signal from a detection chamber (downstream of the illustrated filter arrangement) provides an indication of background light.

Figure 6A:
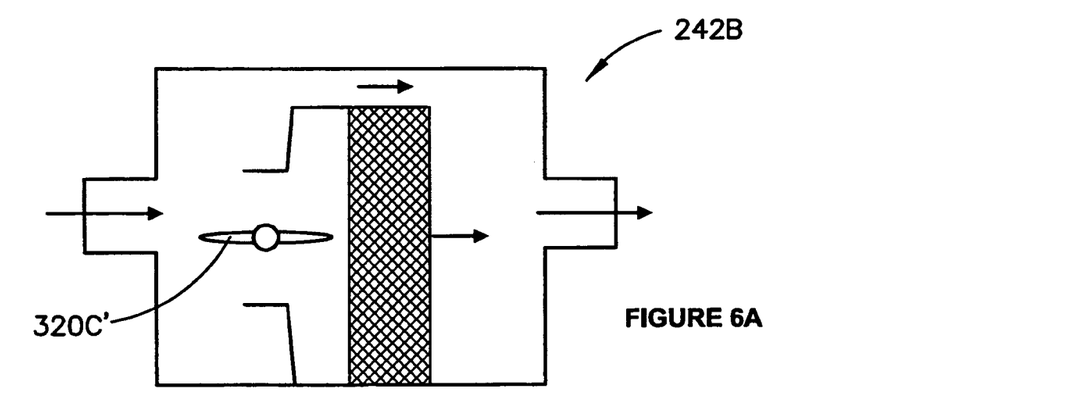
FIG. 6A is a schematic illustration of a filter arrangement according to a further embodiment of the invention in one operating mode.
Figure 6B:
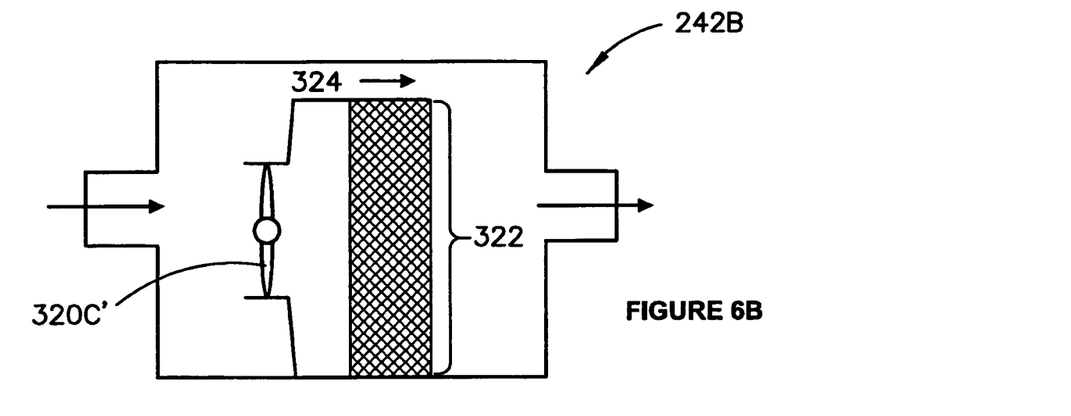
FIG. 6B is a schematic illustration of the filter arrangement of FIG. 3A in another operating mode.
Figure 7:
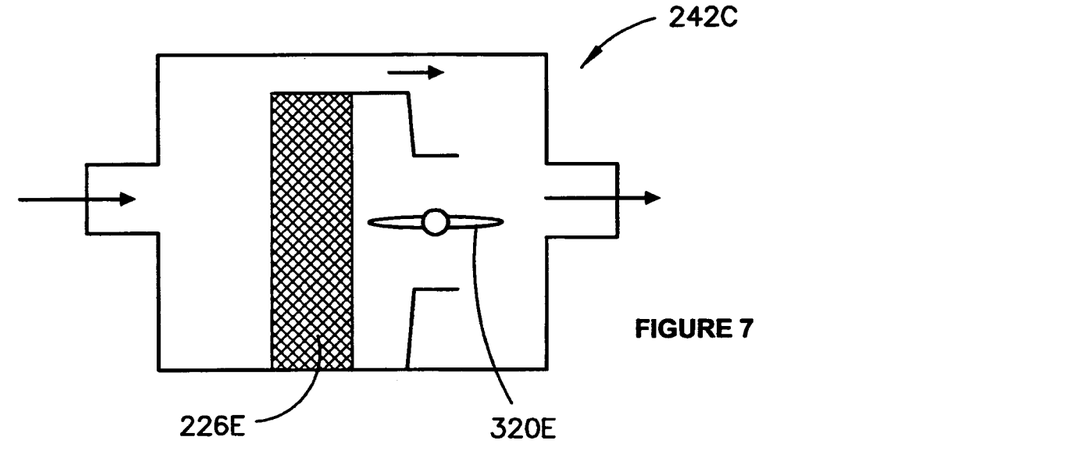
FIG. 7 is a schematic illustration of a fitter arrangement according to a further embodiment of the invention in one operating mode.

FIGS. 6A and 6B illustrate an alternative arrangement wherein the controllable mechanism, in form of flap 320C', is arranged to selectively close the filtered flow path 322, to provide an indication of the condition of the filter 226' the dilution ratio. FIG. 6A shows this configuration in normal use, where the filtered air combines with the bypass air causing a dilution of the amount of particulate outlet flow compared with the inlet flow.

In FIG. 6B the flow through the filter is substantially blocked allowing only undiluted air to pass through the outlet. Thus by blocking flow path 324 when required, the actual inlet particulate concentration may be measured and then compared with the concentration measured when the filtered flow path 322 is not blocked. In this way the dilution factor of the overall filter may be determined and then the threshold levels or sensitivity gain of subsequent analysing equipment may be adjusted.

The skilled person will appreciate that a number of valving arrangements may be used. The applicant contemplates that valve life may be extended by placing the valve down stream of the filter to shield the valve from the dust and debris such as the arrangement illustrated in FIG. 7 wherein the valve 320E is positioned downstream of the filter 226E.

The invention has been described with reference to embodiments having substantially unfiltered bypass flow paths. It is anticipated that these unfiltered bypass flow paths might be spanned by a coarse filter to filter out very large particulate matter, e.g. insects, and for present purposes such an arrangement would be considered substantially unfiltered.

Moreover, the skilled person will appreciate that there are commercially advantageous embodiments which do not include an unfiltered bypass. By way of example, with reference to FIG. 1, both flow paths 22 and 24 might be spanned by identical foam filters (which, when new, filter out dust but not smoke). In this case, in one possible configuration, one of the filters might be only exposed to fluid, and the particulate matter borne thereby, during the filter check mode. The filter check mode being typically brief and infrequent compared to the routine operation in the normal, detection, mode. Therefore, it can be assumed that this filter is operating as in an "as new" condition whilst receiving flow to check the condition of the other filter.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A filter arrangement for a particle detector for detecting particles in an environment, the particle detector including one or more sensors for analyzing fluid in a detection region to produce sensor output indicative of particle concentration, the filter arrangement including:
    structure defining flow paths, for conveying fluid from the environment towards the detection region, including a first flow path, which includes a filter, and a second flow path bypassing the filter;
    a controllable mechanism for adjusting relative flow rates of fluid through the first flow path and the second flow path, by varying relative flow restriction of the first flow path and the second flow path; and
    a controller configured to receive the sensor output indicative of particle concentration at at least two relative flow rates and apply logic thereto to generate an output indicative of a condition of the filter.

2. The filter arrangement of claim 1 wherein the sensor output is indicative of particle concentration.

3. The filter arrangement of claim 1 wherein the mechanism is configured or controlled to vary the relative flow rates, and the controller is configured to produce the output indicative of the condition of the filter, periodically.

4. The filter arrangement of claim 1 wherein the mechanism is configured or controlled to vary the relative flow rates, and the controller is configured to produce the output indicative of the condition of the filter, in response to a sensed variation in particle concentration.

5. The filter arrangement of claim 1 wherein the controller is configured to generate a fault signal if the condition of the filter exceeds a predetermined threshold.

6. The filter arrangement of claim 1 wherein the mechanism is configured or controlled to vary the relative flow rates based on a predicted level of pollution in the environment to control the concentration of pollution reaching the detection region.

7. The filter arrangement of claim 1 wherein the mechanism is configured or controlled to periodically temporarily increase the relative flow rate through the second flow path to periodically increase sensitivity of the detector whereby a time averaged exposure of the detection region to fluid from the second flow path, and contaminants carried thereby, is reduced for reduced contamination of the detection region.

8. The filter arrangement of claim 1 wherein the structure includes any one or more of:
    a flow splitting arrangement to receive a common stream of fluid from the environment and direct respective portions of the stream into the first flow path and the second flow path; and
    a flow combining arrangement to receive fluid from the first flow path and the second flow path and convey a combined stream of fluid toward the detection region.

9. The filter arrangement of claim 1 wherein the structure and mechanism together impose a flow restriction substantially greater than a flow restriction imposed by the filter whereby the relative flow rates through the first flow path and the second flow path are substantially independent of filter condition.

10. The filter arrangement of claim 1 wherein the filter is a HEPA filter.

11. The filter arrangement of claim 1 wherein the second flow path is configured such that fluid carried thereby is substantially unfiltered of particles of interest.

12. A particle detector, for detecting particles in an environment, including:
    structure defining a detection region;
    one or more sensors for analyzing fluid in the detection region to produce sensor output indicative of particle concentration; and
    the filter arrangement of claim 1 arranged to convey fluid, from the environment to the detection region, and to cooperate with the sensors.

13. The particle detector of claim 12 including:
    a controller having a purge mode in which the controller controls the mechanism to deliver fluid to the detection region substantially only from the first flow path to purge the detection region of fluid from the second flow path, and
    a detection mode in which the controller controls the mechanism to deliver at least some fluid from the second flow path to the detection region; and
    being configured to apply logic to sensor output from the detection mode to generate a further output; and if necessary adjust the logic, based on the sensor output from the purge mode, to compensate for contamination of the detection region.

14. A filter arrangement for a particle detector for detecting particles in an environment, the particle detector including one or more sensors for analyzing fluid in a detection region to produce sensor output indicative of particle concentration, the filter arrangement including:
    structure defining flow paths, for conveying fluid from the environment towards the detection region, including a first flow path, which includes a filter, and a second flow path bypassing the filter; and
    a controllable mechanism for adjusting relative flow rates of fluid through the first flow path and the second flow path, by varying relative flow restriction of the first flow path and the second flow path;
    the mechanism being configured or controlled to vary the relative flow rates based on a predicted level of pollution in the environment to control the concentration of pollution reaching the detection region.

15. The filter arrangement of claim 14 wherein the varying the relative flow rates based on the predicted level of pollution includes varying the relative flow rates based on a repeating schedule.

16. The filter arrangement of claim 15 wherein the schedule includes a night mode, in which a relatively lower proportion of fluid passes through the first flow path for relatively higher detector sensitivity, and a day mode in which a relatively higher proportion of fluid passes through the first flow path for reduced contamination of the detection region.

17. The filter arrangement as claimed in claim 14 wherein a mechanism to vary the relative flow rates based on a predicted level of pollution in the environment to control the concentration of pollution reaching the detection region has at least a first mode and second mode corresponding to differing relative flow rates through the first flow path and the second flow path; and
    is configured to switch between said modes based on a predicted level of pollution in the environment to control the concentration of pollution reaching the detection region.

18. The filter arrangement of claim 14 wherein the second flow path is configured such that fluid carried thereby is substantially unfiltered of particles of interest.

19. A filter arrangement for a particle detector for detecting particles in an environment, the particle detector including one or more sensors for analyzing fluid in a detection region to produce sensor output indicative of particle concentration, the filter arrangement including:
structure defining flow paths, for conveying fluid from the environment towards a detection region, including a first flow path, which includes a filter, and a second flow path bypassing the filter;
a controllable mechanism for adjusting relative flow rates of fluid through the first flow path and the second flow path by varying relative flow restriction of the first flow path and the second flow path; and
a controller configured to control the mechanism to periodically temporarily increase the relative flow rate through the second flow path to periodically increase sensitivity of the detector whereby a time averaged exposure of the detection region to fluid from the second flow path, and contaminants carried thereby, is reduced for reduced contamination of the detection region.

20. The filter arrangement of claim 19 wherein the relative flow rate through the second flow path is temporarily increased one or more times per minute.

21. The filter arrangement of claim 19 wherein the mechanism is configured or controlled such that, during each periodic temporary increase in relative flow rate through the second flow path, substantially all of the fluid is conveyed via the second flow path.

22. The filter arrangement of claim 19 wherein the mechanism is configured or controlled such that, between each periodic temporary increase in relative flow rate through the second flow path, substantially all of the fluid is conveyed via the first flow path.

23. The filter arrangement of claim 19 wherein the second flow path is configured such that fluid carried thereby is substantially unfiltered of particles of interest.

24. A particle detector, for detecting particles in an environment, including:
structure defining flow paths, for conveying fluid from the environment towards a detection region, including a first flow path, which includes a filter, and a second flow path bypassing the filter;
a mechanism for controlling relative flow rates of fluid through the first flow path and the second flow path; and
one or more sensors for analyzing fluid in the detection region to produce sensor output; and
a controller having
a purge mode in which the controller controls the mechanism to deliver fluid to the detection region substantially only from the first flow path to purge the detection region of fluid from the second flow path, and
a detection mode in which the controller controls the mechanism to deliver at least some fluid from the second flow path to the detection region; and being configured to apply logic to sensor output from the detection mode to generate a further output; and if necessary adjust the logic, based on the sensor output from the purge mode, to compensate for contamination of the detection region.

25. The particle detector of claim 24 wherein the controller is configured to periodically transition between the purge and detection modes.

26. The particle detector of claim 24 wherein controller is configured such that the transition from the detection mode to purge mode is conditional on the sensor output.

27. The particle detector of claim 24 wherein the controller stores a plurality of measurements based on the sensor output over an interval of time when the chamber is purged.

28. The particle detector of claim 24 wherein the controller is to configured apply further logic, to the sensor output when the chamber is purged, and if necessary generate fault signal.

29. The particle detector of claim 24 wherein the logic includes subtracting a measure of background light from the sensor output.

30. The particle detector of claim 29 wherein the adjusting the logic includes calculating and substituting a new measure of background light.

31. The particle detector of claim 24 wherein the sensors include one or more photoelectric devices.

32. A particle detection system for detecting particles in an environment including:
plumbing defining at least one inlet, for receiving fluid from the environment, and at least one outlet;
an aspirator between the inlet and the outlet to move fluid through the plumbing; and
the particle detector of claim 24 arranged to receive fluid from downstream of the aspirator and deliver fluid upstream of the aspirator whereby fluid is moved through the particle detector by the aspirator.

33. A method of determining a condition of a filter in a particle detector, the particle detector including structure defining flow paths for conveying fluid from a monitored environment towards a detection region of the particle detector, said structure including a first flow path which includes the filter and a second flow path which bypasses the filter, said particle detector including one or more sensors for analyzing the fluid in the detection region to produce sensor output indicative of particle concentration, the method including:
adjusting relative flow rates of fluid through the first flow path and the second flow path;
obtaining sensor output indicative of particle concentration at at least two relative flow rates; and
applying logic to the sensor output to generate an output indicative of a condition of the filter.

34. A method of determining filter condition of a filter of a particle detector, the particle detector including structure defining flow paths for conveying fluid from a monitored environment towards a detection region of the particle detector, said structure including a first flow path which includes the filter and a second flow path which bypasses the filter, said particle detector including one or more sensors for analyzing the fluid in the detection region to produce sensor output indicative of particle concentration, the method including:
adjusting relative flow rates of fluid through the first flow path and the second flow path; and
periodically temporarily increasing the relative flow rate through the second flow path to periodically increase sensitivity of the detector whereby a time averaged exposure of the detection region to fluid from the second flow path, and contaminants carried thereby, is reduced for reduced contamination of the detection region.

* * * * *